United States Patent [19]

Pittendrigh

[11] Patent Number: 5,273,967
[45] Date of Patent: Dec. 28, 1993

[54] METHOD OF MOSQUITO CONTROL

[76] Inventor: Barry R. Pittendrigh, 19 Merlin Crescent, Regina, Saskatchewan, Canada, S4R 3E1

[21] Appl. No.: 749,728

[22] Filed: Aug. 26, 1991

[51] Int. Cl.⁵ .............. A01N 25/26; A01N 43/04; A01N 57/00
[52] U.S. Cl. .............. 514/54; 514/57; 424/93 K; 424/93 L; 424/405; 424/489
[58] Field of Search .............. 424/405, 93 L, 93 K, 424/489; 514/54, 57

[56] References Cited

U.S. PATENT DOCUMENTS

| | | | |
|---|---|---|---|
| 871,612 | 11/1907 | Nesfield | 424/405 |
| 2,109,642 | 3/1938 | Hunt | 43/124 |
| 3,150,062 | 9/1964 | Greenberg et al. | 424/93 L |
| 3,285,748 | 11/1966 | Koonz et al. | 424/93 L |
| 3,702,359 | 11/1972 | Dulmage et al. | 424/93 L |
| 3,911,110 | 10/1975 | Smirnoff | 424/93 L |
| 4,160,033 | 7/1979 | Garrett et al. | 514/473 |
| 4,166,112 | 8/1979 | Goldberg | 424/93 L |
| 4,187,290 | 2/1980 | Goldberg | 424/93 L |
| 4,228,614 | 10/1980 | Cardarelli | 514/89 |
| 4,376,113 | 3/1983 | Suglia et al. | 424/93 L |
| 4,401,456 | 8/1983 | Connick | 424/488 |
| 4,563,344 | 1/1986 | Kotz et al. | 424/93 L |
| 4,569,947 | 2/1986 | Stockton et al. | 514/724 |
| 4,631,857 | 12/1986 | Kase et al. | 43/132.1 |
| 4,647,578 | 3/1987 | Crounse et al. | 514/454 |
| 4,650,792 | 3/1987 | Underwood | 514/107 |
| 4,707,359 | 11/1987 | McMullen | 71/3 |
| 4,762,718 | 8/1988 | Marks | 424/405 |
| 4,774,074 | 9/1988 | Snipes | 424/405 |
| 4,818,534 | 4/1989 | Levy | 424/484 |
| 4,861,754 | 8/1989 | Farkas-Himsley | 424/405 |
| 4,888,325 | 12/1989 | Schroeder et al. | 424/405 |
| 4,983,389 | 1/1991 | Levy | 424/405 |
| 4,983,390 | 1/1991 | Levy | 424/405 |
| 4,983,583 | 1/1991 | Ridoux | 514/54 |
| 4,985,251 | 1/1991 | Levy | 424/405 |
| 4,992,275 | 2/1991 | Lush | 424/405 |
| 5,061,697 | 10/1991 | Shasha et al. | 424/405 |

OTHER PUBLICATIONS

The Merck Index, An, Encyclopedia of Chemicals, Drugs, and Biologicals, Tenth Edition, Windholz, Editor, published by Merck & Co., Inc., Rahway, N.J., U.S.A., 1983, pp. 229-230.

*Primary Examiner*—Ronald W. Griffin
*Attorney, Agent, or Firm*—Murray E. Thrift; Stanley G. Ade; Adrian D. Battison

[57] ABSTRACT

A process is described for the control of the development of mosquitos in a body of water, by spreading on the body of water a particulate carbohydrate compound. The carbohydrate compound may be a given compound that forms a hydrophillic gum-like layer once spread on the surface of the water. The gum-like layer prevents the development of mosquito in the larvae and pupae stages. It is also believed to inhibit the laying of eggs on the water surface by the female mosquito. The layer found is environmentally safe as the carbohydrates used are common in food products.

8 Claims, No Drawings

METHOD OF MOSQUITO CONTROL

FIELD OF THE INVENTION

This invention relates to the field of insecticides, more particularly to the destruction of mosquito pupae and larvae.

BACKGROUND OF THE INVENTION

There are insecticides available today that destroy the mosquito at the larval or pupal stage. In most cases, the pests are dealt with by the use of chemical insecticides or varieties of the microorganism *Bacillus thuringiensis*. Some well known chemicals used in mosquito control are methoxychlor, malathion, methophrine, diflurbenzuron and diflorbensuron. The use of chemicals is effective and widely used, however there are many well known negative environmental side effects associated with their use. The conventional technique for mosquito control is to apply the chemicals, often in a floating format, to contact and poison the larvae and pupae floating at the surface of a body of water.

Other techniques for the destruction of mosquito larvae and pupae include those described in the following:

U.S. Pat. No. 4,569,947 describes a method in which a beta alcohol organic compound, is spread on a body of water containing mosquito larvae and pupae, to control the larvae and pupae.

U.S. Pat. No. 4,707,359 describes a system in which a water surface is covered with a layer comprising an insoluble mono-molecular compound, an insoluble foam or a duplex film, and a layer of larvae toxic chemical to control mosquitoes in their early stages.

U.S. Pat. No. 4,228,614 describes a system in which hydrocarbon polymers such as ethylene-propylene and ethylenevinyl acetate compounds, along with a pesticide, are spread on the surface of a body of water to control mosquito larvae and pupae.

All of the above techniques use chemical insecticides that can be considered detrimental to the environment. The present invention is concerned with an alternative mosquito control system.

SUMMARY OF THE INVENTION

According to one aspect of the present invention there is provided a process for the control of the development of mosquitoes in a body of water comprising spreading on the surface of the body of water a particulate carbohydrate compound.

According to another aspect of the present invention there is provided a process for the inhibition of the propagation of mosquitoes in a body of water comprising spreading on the surface of the body of water a particulate carbohydrate compound.

The carbohydrate compound, which may be a gum compound, forms a thin hydrophillic gum-like layer once spread on the surface of the body of water.

This hydrophilic gum-like layer dissipates within a short time, say one week, and breaks down into its environmentally safe molecular carbohydrate components.

The film that forms on the surface of the body of water is thick enough to prevent the air tubes of the immature mosquito, in the larval or pupal form, from reaching the air above the surface of the water. As a result, the creature is unable to obtain oxygen and it suffocates, dies and typically sinks to the bottom of the body of water. (Appendix 1).

DETAILED DESCRIPTION

Compounds useful in practising the invention include, but are not limited to, long chain polysaccharides, long chain heteropolysaccharides, long chain structural polysaccharides for example:

Xanthan gum
Algin (salts of alginic acid)
Agar
Guar gum
Cellulose
Sodium carboxymethylcellulose
Methyl cellulose
Hydroxyethyl cellulose
Hydroxypropyl cellulose
Locust Beam Gum
Gum Carrageenan
Gum Tragacanth
Bran
Gum Accroides
Gum Arabic
Gum Dammar
Gum Eleni
Gum Ghatti
Gum Guaiac
Gum Kakaya
Gum Mastic
Gum Pontiamak
Gum Rosim
Gum Storax
Tamarind Gum
Psyllium Seed Gum
Larch Gum
Pectins
Propylene glycol alginate
S-194
and mixtures thereof Most of the above materials are environmentally safe and approved for use in food products. Many are also inexpensive and very easy to use.

When spread substantially uniformly on the surface of the body of water, each of the materials, with the exception of bran and cellulose, absorbs water, swells and forms a layer extending up to several millimeters into the water. This prevents the mosquito larvae and pupae from reaching the air above the water to breathe, resulting in larvae and pupae death. The bran, when used, aids in the spreading capacity of the compounds, when they are applied to the surface of the water. Although cellulose is not soluble in water, it will form a temporary layer on and slightly below the surface of the water.

The application of the xanthan gum and bran has also demonstrated an effect on the development of mosquito eggs. It has been found that the spreading of the polysaccharide compound xanthan gum and bran on the body of water reduces the numbers of mosquito larvae that successfully emerge from their floating egg pods.

It is believed that the application of the above compound will also inhibit the laying of eggs on the water surface by the female mosquito, as the mosquito "tests" the water with the bottom of her legs before she lays her eggs. If these compounds, or mixtures thereof, are on the surface of the water, it is believed that the female mosquito will not lay her eggs.

The application of the above compound may also be done in conjunction with conventional insecticide chemicals or microorganisms.

Qualitative testing was conducted as described in the following examples and appendices:

EXAMPLES

ONE. A body of water with 0.1 square meter surface contained twenty mosquito larvae and twenty mosquito pupae. Two grams of a compound mixture consisting of two parts Xanthan Gum to one part fine ground bran in particulate form were spread on the surface of the water. The compound mixture immediately formed a layer on the surface of the water, which extended one to two millimeters into the water. Within ten minutes the compound mixture formed a layer three to ten millimeters which extended below the water surface. If left undisturbed the material took a week to settle out (Appendix two). When the surface layer was disturbed by repeated droplets of water, the compound mixture (two parts Xanthan Gum to one part fine ground bran) settled out immediately (Appendix Four). A through examination of the water revealed no living mosquito larvae or pupae (Appendix One). Dead larvae and pupae were usually found at the bottom of the body of water.

TWO. The procedure as described in Example 1 was repeated using two grams of a mixture of four parts Xanthan Gum and one part Algin. The mortality rate of the larvae and pupae after 24 hours were 85% and 100%, respectively (Appendix one). This compound did not dissipate into the water within seven days after its application (Appendix Two). As an Example 1, this chemical dissipated into the water when the layer was repeatedly struck by droplets of water (Appendix 4).

APPENDIX ONE—EFFECTS ON LARVAE/PUPAE MORTALITY RATES

Purpose

Experiments were performed in order to test the effects of the mixtures on the mortality rates of last instar mosquito larvae and mosquito pupae.

Materials and Methods i. Approximately 207 test ponds were prepared in the following fashion. Eight liters of boiled tap water were placed in each pond (a dish pan); each pan had a surface area of 0.1 squared meters. The water was left standing for 24 hours.

ii. As mosquito larvae became available from ponds found in Saskatchewan, the experiments were performed. Twenty larvae and pupae were typically placed in each pond. In some cases only larvae or pupae were tested. The ponds were then treated with the test mixtures. Two grams of the mixture were held 30 centimeters above the ponds surface. The container holding the mixture was gently shaken and moved around above the pond to assure even distribution of the compound mixture. Tests of each of the mixtures were repeated throughout the summer. With each set of tests, controls were performed. The compounds used in the mixtures included Algin, fine ground bran, Sodium carboxymethylcellulose, Gum Xanthan and Gum Guar.

iii. After 24 hours, the mortality rates of the ponds were recorded. The living mosquito "larvae and pupae were removed from the containers and counted.

Results

SUMMARY OF DATA

| CHEMICAL MIXTURE OF MIXTURE | LARVAE MORTALITY | NUMBER OF TRIALS | PUPAE MORTALITY | NUMBER TRIALS |
| --- | --- | --- | --- | --- |
| 3 ALGIN/1BRAN | 72.0% | 5 | 95% | 4 |
| 2 ALGIN/1BRAN | 81.3% | 4 | 95% | 4 |
| 1 ALGIN | 74.0% | 2 | 100% | 3 |
| 1 ALGIN/1BRAN | 53.8% | 4 | 51.3% | 4 |
| 1 XANTHAN (KELTROL F) | 86.7% | 3 | 100% | 3 |
| 1 XANTHAN | 77.5% | 2 | 100% | 2 |
| 3 XANTHAN/1BRAN | 96.7% | 6 | 100% | 6 |
| 2 XANTHAN/1BRAN | 100.0% | 4 | 100% | 4 |
| 1 XANTHAN/1ALGIN | 88.8% | 4 | 100% | 4 |
| 2 XANTHAN/1ALGIN | 46.7% | 3 | 95% | 2 |
| 3 XANTHAN/1ALGIN | 87.5% | 4 | 100% | 4 |
| 4 XANTHAN/1ALGIN | 85.0% | 5 | 100% | 4 |
| 1 XANTHAN/1 ALGIN | 51.7% | 3 | 100% | 4 |
| 1 XANTHAN/2 ALGIN | 51.7% | 3 | 100% | 4 |
| 1 XANTHAN/3 ALGIN | 58.8% | 4 | 97.5% | 4 |
| 1 XANTHAN/4 ALGIN | 52.5% | 4 | 97.5% | 4 |
| 1 XANTHAN/1 CMC | 61.3% | 4 | 87.5% | 4 |
| 1 XANTHAN/2 CMC | 38.8% | 6 | 55.0% | 6 |
| 1 XANTHAN/3 CMC | 25.0% | 3 | 39.0% | 5 |
| 1 XANTHAN/4 CMC | 2.0% | 5 | 40.0% | 5 |
| 2 XANTHAN/1 CMC | 52.0% | 5 | 90.0% | 5 |
| 3 XANTHAN/1 CMC | 51.0% | 5 | 88.0% | 5 |
| 4 XANTHAN/1 CMC | 67.0% | 5 | 98.0% | 5 |
| 1 XANTHAN/1 GUAR | 93.3% | 6 | 100.0% | 6 |
| 1 XANTHAN/2 GUAR | 85.7% | 7 | 100.0% | 6 |
| 2 XANTHAN/1 GUAR | 85.7% | 7 | 100.0% | 7 |
| 3 XANTHAN/1 GUAR | 74.4% | 9 | 100.0% | 9 |
| 1XANTHAN/1 ALGIN/1 BRAN | 88.0% | 5 | 100.0% | 5 |
| 2XANTHAN/2 ALGIN/1 BRAN | 76.3% | 4 | 97.5% | 4 |
| 3XANTHAN/2 ALGIN/1 BRAN | 79.4% | 8 | 100.0% | 5 |
| 2XANTHAN/3 ALGIN/1 BRAN | 68.8% | 4 | 100.0% | 4 |
| 3XANTHAN/1 ALGIN/1 BRAN | 82.5% | 2 | 100.0% | 2 |
| 1 CMC/4 ALGIN | 21.0% | 5 | 95.0% | 5 |
| 2XANTHAN/1 GUAR/1 BRAN | 95.7% | 7 | 100.0% | 7 |
| 3XANTHAN/1 GUAR/1 BRAN | 90.6% | 9 | 100.0% | 9 |

-continued

| CHEMICAL MIXTURE OF MIXTURE | SUMMARY OF DATA LARVAE MORTALITY | NUMBER OF TRIALS | PUPAE MORTALITY | NUMBER TRIALS |
| --- | --- | --- | --- | --- |
| CONTROL | 1.3% | 36 | 0.2% | 33 |

KEY
CMC - Sodium carboxymethylcellulose
BRAN - Finely ground bran
GUAR - Gum Guar
XANTHAN - Gum Xanthan Conclusions Many of the chemical mixtures, as shown in the results section, showed extremely high mortality rates.

APPENDIX TWO—DISSIPATION RATES OF CHEMICALS

Purpose

Experiments were performed in order to test the dissipation rates of some of the chemical mixtures given in Appendix One.

Materials and Methods i. Eleven test ponds were prepared in the following fashion. Eight liters of boiled tap water were placed in each pond (dish pan); each pan had a surface area of 0.1 squared meters. The water was left standing for 24 hours.

ii. A particular test chemical mixture was placed on each of the ponds. Two grams of test chemicals were used in each test. These chemical mixtures included 3 Gum Xanthan/1 fine ground bran (F. G. Bran)/1 Gum Guar, 2 Gum Xanthan/1 Algin, 2 Gum Xanthan/3 Algin/1 fine ground bran, 4 Gum Xanthan/1 Algin, 1 Algin/1 fine ground bran, 4 Algin/1 Sodium carboxymethylcellulose (CMC), 1 Gum Xanthan/4 CMC, 1 Gum Xanthan/2 Gum Guar, 2 Gum Xanthan/1 fine ground bran, 3 Gum Xanthan/1 Gum Guar, and 1 Gum Xanthan/2 CMC.

iii. Dissipation of the chemicals was observed over a one week period. If the layer had not dissipated by one week then the following procedure was performed. The experimenter placed his/her mouth at a 15 centimeters distance from the surface of the crater. The experimenter then blew on the layer with as much force as possible. This tested the strength of the layer after one week. Qualitative observations of this layer were also recorded.

Results

| CHEMICAL COMBINATION | DISSIPATION DATE | DESCRIPTION OF LAYER |
| --- | --- | --- |
| 3 XANTHAN/ 1 F.G. BRAN/ 1 GUM GUAR | Not dissipated by seventh day | Thin layer still remained |
| 2 XANTHAN/ 1 ALGIN | Not dissipated by seventh day | Thick layer across all of the pond/broken by heavy blowing at 15 cm |
| 2 XANTHAN/ 3 ALGIN/ 1 F.G. BRAN | Not dissipated by seventh day | Layer could be broken by blowing at 15 cm |
| 4 XANTHAN/ 1 ALGIN | Not dissipated by seventh day | Layer could be broken by blowing at 15 cm |
| 1 ALGIN/ 1 F.G. BRAN | Not dissipated by seventh day | Layer could not be broken by blowing at 15 cm |
| 1 ALGIN/ 1 CMC | Not disspated by seventh day | Layer could not be broken by blowing at 15 cm/highly durable layer |
| 1 XANTHAN/ 4 CMC | Dissipated in thirty minutes | |
| 1 XANTHAN/ 2 GUM GUAR | Dissipated in six days | |
| 2 XANTHAN/ 1 F.G. BRAN | Dissipated in seven days | Some finely ground bran remained on the surface |
| 3 XANTHAN/ 1 GUM GUAR | Dissipated in seven days | |
| 1 XANTHAN/ 2 CMC | Dissipated in a day | |

Conclusions

The dissipation rates were variable depending on the chemical mixtures. Same of the mixtures were persistent after seven days.

APPENDIX THREE—MOSQUITO EGG TESTS

Purpose

Experiments were performed in order to test the ability of the compound mixture, 2 parts Gum Xanthan and 1 part finely ground bran, for its ability to reduce the survival rate of larvae emerging from floating mosquito egg pods (or to reduce the number of larvae emerging from the eggs pods).

Materials and Methods i. Twenty tests ponds were prepared in the following fashion. Eight liters of boiled tap water were placed in each pond (dish pan); each pan had a surface area of 0.1 squared meters. The water was left standing for 24 hours.

ii. Eleven mosquito egg pods were collected from the pond surfaces. Each egg pod was divided into separate halves and placed in a separate pond. One pond acted as the control and the other pond was treated with the test chemical. In test pond ten, two eggs pods were used. Half of each pod was placed in each tray.

iii. In tests one to four the eggs were placed on the pond. Then, the chemical mixture (2 parts Gum Xanthan and one part finely ground bran) was applied to the surface immediately afterwards.

iv. In tests five to ten, the chemicals (2 parts Gum Xanthan and one part finely ground bran) were placed on first, then the egg pods were gently placed on this film immediately afterwards (simulating a female mosquito laying eggs).

v. The results were recorded two to four days afterwards, depending on when the larvae in the control tray were large enough to be counted. If no larvae were present in the control by the third day, the experiments were halted.

vi. Those tests in which the control trays yielded no larvae, the results were not taken into consideration in the calculation of the final averages.

Results

TABLE ONE

| TRIAL NUMBER | CHEMICAL FIRST | EGG POD FIRST | LENGTH OF TEST | NUMBER OF LARVAE PRESENT |
|---|---|---|---|---|
| 1 | X | | 4 days | 0 Larvae |
| Control | | | 4 days | 47 Larvae |
| 2 | | X | 4 days | 3 Larvae |
| Control | | | 4 days | 23 Larvae |
| 3 | X | | 3 days | 0 Larvae |
| Control | | | 3 days | 0 Larvae |
| 4 | X | | 3 days | 0 Larvae |
| Control | | | 3 days | 0 Larvae |
| 5 | X | | 3 days | 0 Larvae |
| Control | | | 3 days | 0 Larvae |
| 6 | X | | 3 days | 0 Larvae |
| Control | | | 3 days | 0 Larvae |
| 7 | | X | 3 days | 0 Larvae |
| Control | | | 3 days | 0 Larvae |
| 8 | | X | 3 days | 0 Larvae |
| Control | | | 3 days | 0 Larvae |
| 9 | | X | 3 days | 55 Larvae |
| Control | | | 3 days | 96 Larvae |
| 10 | X | | 2 days | 2 Larvae |
| Control | | | 2 days | 48 Larvae |

TABLE TWO

Summary of Results

| NUMBER OF SUCCESSFUL TRIALS | EGGS FIRST | CHEMICALS FIRST | AVERAGE NUMBER OF LARVAE PRESENT AT THE END OF THE TEST | SIGNIFICANT AT 0.05 LEVEL |
|---|---|---|---|---|
| 2 | X | | 29.0 Larvae | No |
| Control | | | 59.5 Larvae | |
| 2 | | X | 1.0 Larvae | Yes |
| Control | | | 47.5 Larvae | |

Conclusions

When the ponds were treated with the compound (2 parts Gum Xanthan and 1 part finely ground bran) before the egg pods were placed on the surface, the levels of larvae were significantly reduced.

APPENDIX FOUR—SIMULATED RAIN TESTS

Purpose

Experiments were performed in order to test the effects of simulated rain on the surface gum layers in a pond situation.

Materials and Methods i. Five test ponds were prepared in the following fashion. Eight liters of boiled tap water were placed in each pond (dish pan); each pan had a surface area of 0.1 squared meters. The water was left standing for 24 hours.

ii. In this test, rain was simulated by using a 1.3 liter cup with 50 pin sized holes in the bottom. Two grams of the chemical mixture, 2 parts Gum Xanthan/1 part finely ground bran, was placed on the test pond. After one hour the cup was filled with 500 mls of water and held 20 centimeters above the pond surface. The cup was moved around to assure equal distribution of the "rain water" on the pond.

iii. Procedure two was repeated in the four other ponds using the following chemical mixtures: 1 Algin/1 CMC, 4 Gum Xanthan/1 Algin, 2 Algin/1 fine ground bran, and 2 Gum Xanthan/1 fine ground bran.

Results

In all the tests the simulated rain water caused breaking up of the surface gum layer. Much of the gum layer in turn dissipated or fell to the bottom of the pond.

Conclusion

The results suggest that when the gum layer is exposed to a rain-like situation that the layer would be dispersed immediately.

I claim:

1. A method for killing immature mosquitoes in a body of water comprising spreading on the surface of the body of water a particulate, solid carbohydrate compound that is non-soluble in water and capable of hydrating, the compound being spread in a quantity sufficient to hydrate at the surface of the body of water and form a substantially unbroken, floating hydrated carbohydrate layer of sufficient thickness to retain the mosquitoes below the surface of the body of water and out of contact with air above the surface of the body of water thereby suffocating the mosquitoes in the body of water.

2. A method according to claim 1 in which the particulate carbohydrate compound is a long chain polysaccharide compound.

3. A method according to claim 2 in which the particulate carbohydrate compound is a long chain heteropolysaccharide.

4. A method according to claim 3 in which the particulate carbohydrate compound is a long chain structural heteropolysaccharide.

5. A method according to claim 1 in which the particulate carbohydrate compound is selected from the group consisting of:

Xanthan gum
Algin and salts of alginic acid
Agar
Guar gum
Cellulose
Sodium carboxymethylcellulose
Methyl cellulose
Hydroxyethyl cellulose
Hydroxypropyl cellulose
Locust Bean Gum
Gum Carrageenan
Gum Tragacanth
Gum Accroides
Gum Arabic
Gum Dammar
Gum eleni
Gum Ghjatti
Gum Guaiac
Gum Kakaya
Gum Mastic
Gum Pontiamak
Gum Rosin
Gum Storax
Tamarind Gum
Psyllium Seed Gum
Larch Gum
Pectins
Propylene Glycol Alginate
S-194 and mixtures thereof.

6. A method according to claim 1 in which the mosquito is in its egg larvae or pupae stages.

7. A method according to claim 1 in which the particulate carbohydrate compound is used in combination with a chemical insecticide.

8. A method according to claim 1 in which the particulate carbohydrate compound is used in combination with an insecticidal microorganism.

* * * * *